(12) United States Patent
Reinbold

(10) Patent No.: US 9,119,695 B2
(45) Date of Patent: Sep. 1, 2015

(54) REPLACEABLE HEAD PART FOR AN ELECTRIC TOOTHBRUSH

(75) Inventor: Klaus Reinbold, Buehl (DE)

(73) Assignee: GlaxoSmithKline Consumer Healthcare GMBH & CO. KG, Buehl (Baden) (DE)

( * ) Notice: Subject to any disclaimer, the term of this patent is extended or adjusted under 35 U.S.C. 154(b) by 264 days.

(21) Appl. No.: 13/825,583

(22) PCT Filed: Sep. 22, 2011

(86) PCT No.: PCT/EP2011/066493
§ 371 (c)(1),
(2), (4) Date: Mar. 22, 2013

(87) PCT Pub. No.: WO2012/038501
PCT Pub. Date: Mar. 29, 2012

(65) Prior Publication Data
US 2013/0180063 A1    Jul. 18, 2013

(30) Foreign Application Priority Data
Sep. 24, 2010 (GB) .................................. 1016209.7

(51) Int. Cl.
*A46B 13/02* (2006.01)
*A61C 17/34* (2006.01)
*A61C 17/22* (2006.01)

(52) U.S. Cl.
CPC ............. *A61C 17/22* (2013.01); *A61C 17/3436* (2013.01); *A46B 13/02* (2013.01); *A61C 17/222* (2013.01)

(58) Field of Classification Search
CPC ................ A61C 17/34–17/3436; A61C 17/32; A46B 13/00; A46B 13/02; A46B 13/008; A46B 13/023; A46B 13/026
USPC ........................................... 15/28, 22.2, 22.1
See application file for complete search history.

(56) References Cited

U.S. PATENT DOCUMENTS

| 6,381,795 | B1 | 5/2002 | Hofmann et al. | |
| 6,421,865 | B1 | 7/2002 | McDougall | |
| 2005/0011023 | A1* | 1/2005 | Chan | 15/22.1 |
| 2005/0150067 | A1* | 7/2005 | Cobabe et al. | 15/22.1 |

FOREIGN PATENT DOCUMENTS

| CH | 688537 A5 | 11/1997 | |
| DE | 202008005856 | 9/2008 | |
| WO | WO 03101337 A1 * | 12/2003 | A61C 17/34 |
| WO | WO 2006/004316 | 1/2006 | |

* cited by examiner

*Primary Examiner* — Mark Spisich
*Assistant Examiner* — Andrew A Horton
(74) *Attorney, Agent, or Firm* — Joshua C. Sanders; Theodore R. Furman

(57) ABSTRACT

A replaceable head part for an electric powered toothbrush comprising an elongate sleeve including a flexible portion, and containing a longitudinal drive shaft rotatable in oscillatory rotary motion. The drive shaft has a spherical bearing part received in a cavity in the sleeve. The head part incorporates a transmission system to convert the rotation of the head drive shaft into rotation of the bristle carrier comprising an eccentric pin extending from the head drive shaft to move the bristle carrier in oscillatory rotary motion, and having a spherical pin bearing part received in a receiving cavity in the bristle carrier.

16 Claims, 3 Drawing Sheets

REPLACEABLE HEAD PART FOR AN ELECTRIC TOOTHBRUSH

This application is a 371 of International Application No. PCT/EP2011/066493, filed 22 Sep. 2011, which claims the priority of GB Application No. GB 1016209.7 filed 24 Sep. 2010, which is incorporated herein in its entirety.

This invention relates to electric toothbrushes, in particular to replaceable head parts for electric toothbrushes.

Electric toothbrushes are well known. Generally electric toothbrushes comprise a handle containing an electric power source such as a replaceable or rechargeable battery and an electric motor powered by the power source. Generally from the handle extends a handle drive shaft, with a transmission means between the motor and the handle drive shaft to cause the drive shaft to rotate with continuous or oscillatory rotary motion. Generally adjacent the handle drive shaft is a connector for a replaceable head part. Typically the handle drive shaft passes through the connector.

Generally replaceable head parts comprise an elongate sleeve having a connection at one longitudinal end to mate with the connector on the handle, a bristle carrier mounting at the opposite longitudinal end with a bristle carrier mounted thereon for continuous or oscillatory rotary motion, generally about a rotation axis transverse to the sleeve longitudinal direction. Generally a head drive shaft extends longitudinally along and within the sleeve part, and has a connection such as a spline socket at its end closest to the connection to connect with the handle drive shaft when the head part is connected to the handle by engagement of the connector and the connection. Generally such a head drive shaft rotates in either continuous or oscillatory rotary motion about a rotation axis generally aligned with the shaft longitudinal direction.

Generally between the head drive shaft and the bristle carrier is a transmission system to convert the rotation of the head drive shaft about the axis generally aligned with the shaft longitudinal direction to the rotation of the bristle carrier about a rotation axis transverse to the shaft longitudinal direction.

Many such toothbrushes are known. For example WO-A-91/07117 discloses a power toothbrush having a transmission system comprising two engaging crown gears. For example U.S. Pat. No. 5,625,916 discloses a commonly used transmission system comprising a rotary head drive shaft that has an off-centre eccentric pin extending in a direction radial to the rotation axis of the head drive shaft, and which engages with a cavity in the side of a cylindrical bristle support so that as the head drive shaft rotates it causes the bristle carrier to rotate in oscillatory rotary motion. DE 202008005856U1 and CH-A-688537 disclose similar systems.

It is also known to provide a replaceable head part for an electric toothbrush which is flexible under the action of pressure applied to the bristle carrier during use of toothbrush. For example EP-A-1 186 254 discloses a head part which includes an elastic flexing zone which divides the sleeve part into two parts on either longitudinal side of the flexing zone. Various other constructions of electric toothbrush head part incorporating flexible zones between the bristle support and handle are known, for example in EP-A-0 510 940.

When the head part is flexible as mentioned above there remains an ongoing problem with the commonly used transmission system mentioned above using an eccentric pin, of optimizing the frictional contact between the pin and the head part and of maintaining uniform forces in the transmission system between the head drive shaft and the bristle carrier. It is an object of the present invention to address this problem.

Other objects and advantages of the present invention will be apparent from the following description.

According to this invention there is provided a replaceable head part for an electric powered toothbrush comprising an elongate sleeve having a connection at one longitudinal end to mate with a connector on an electric toothbrush handle, the sleeve having a bristle carrier mounting at the opposite longitudinal end and having a bristle carrier mounted thereon for rotary motion about a rotation axis transverse to the sleeve longitudinal direction, having a head drive shaft extending longitudinally along the sleeve part and mounted for rotary motion about a rotation axis generally aligned with the sleeve longitudinal direction, characterized in that:

the sleeve incorporates a flexible region which allows the part of the sleeve between the bristle support and flexible region to move relative to the connection under pressure on the bristle carrier during use, adjacent the end of the head drive shaft longitudinally furthest from the connection is a spherical head drive shaft bearing part, and the sleeve has a corresponding head drive shaft bearing part receiving cavity receiving the spherical head drive shaft bearing part, the head part incorporates a transmission system to convert the rotation of the head drive shaft into rotation of the bristle carrier about a rotation axis transverse to the shaft longitudinal direction comprising an eccentric pin extending from the head drive shaft adjacent the end of the head drive shaft longitudinally furthest from the connection to a pin end distanced from the head drive shaft in a direction radial to the rotation axis of the head drive shaft, and having adjacent to the pin end a spherical pin bearing part, the bristle carrier having a spherical pin bearing part receiving cavity therein radially distanced from the rotation axis of the bristle carrier, to receive the spherical pin bearing part, and dimensioned such that when the head drive shaft moves in oscillatory rotary motion about its rotation axis the spherical pin bearing part bears against surfaces of the cavity circumferentially spaced around the rotation axis of the bristle carrier such that the bristle carrier is thereby caused to move in oscillatory rotary motion.

It is found that the provision of the two said spherical bearing parts optimizes the friction between the head drive shaft and the sleeve, and between the pin and the bristle carrier, and helps to maintain uniform forces in the transmission system between the head drive shaft and the bristle carrier as the flexible head part flexes during use.

Preferably the bristle carrier is mounted for oscillatory rotary motion.

Preferably the rotation axis of the bristle carrier is generally perpendicular to the sleeve longitudinal direction, e.g. within 80-90° to the sleeve longitudinal direction. The bristle carrier has a surface from which the bristles extend.

Preferably the head drive shaft is mounted for oscillatory rotary motion.

Preferably the motor and the transmission in the handle are arranged to communicate oscillatory rotary motion to the handle drive shaft.

Preferably the flexible region is located in the longitudinal half of the sleeve closest to the connection. For example such a flexible region may extend from the end of the sleeve closest to the connection for up to 30% of the distance between the connection and the bristle carrier mounting. Preferably the flexible region comprises a composite plastics material— elastomer material region. For example the sleeve may be made of a plastics material such as polypropylene as is common in the art, and may have apertures therein, e.g. passing completely through the plastics material wall of the sleeve, the apertures containing a resiliently flexible elastomer material such as a thermoplastic elastomer material. Such a flexible region may be made by the known process of first injection moulding a plastic material sleeve including such apertures, enclosing the so formed sleeve in a second injection mould, and injecting moulding the elastomer material into the apertures.

Preferably the flexible region allows the part of the sleeve between the bristle support and flexible region to move relative to the connection under pressure on the bristle carrier during use in an arc in a plane parallel to the rotation axis of the bristle carrier. Movement up to 10° for example up to 5° appears to be sufficient to help to relieve excessive brushing pressures during use.

Preferably the head drive shaft is flexibly able to bend as the said part of the sleeve between the bristle support and flexible region moves. The head drive shaft may be made of a flexible plastic material, such as POM (polyoxymethylene). For example the head drive shaft may comprise longitudinally alternating wide and narrow portions to enhance flexibility.

Adjacent, preferably at, the end of the head drive shaft longitudinally furthest from the connection is a spherical head drive shaft bearing part. The term "sphere" and derived terms as used herein includes ellipsoid and oblate spheroid. The head drive shaft bearing part may be spherical over a sufficiently large part of its outer surface that during the flexing movement of the sleeve a spherical surface of the head drive shaft bearing part remains in contact with the bearing cavity. The drive shaft bearing part may comprise an integral part of the drive shaft, or alternately, e.g. to minimise the effect of wear on the bearing, the bearing may be made of metal as a separate part and attached to the drive shaft.

The sleeve bearing receiving cavity which receives the spherical head drive shaft bearing part adjacent the end of the drive shaft may for example be a cylindrical cavity. This may be a plastic sided cavity in a plastic part of the sleeve adjacent to the bristle carrier mounting, but preferably the sleeve bearing receiving cavity is metal-lined, especially if the bearing part is itself made of metal. For example the cavity may be provided by a cylindrical bored insert into the plastic material of the sleeve.

Preferably the eccentric pin extends from the head drive shaft at a position a short distance from the end of the drive shaft closest to the bristle carrier mounting. Preferably the eccentric pin comprises a pin part extending transverse to the head drive shaft in a direction radial to the rotation axis of the head drive shaft, connecting to a pin part extending parallel to the head drive shaft to the pin end. The spherical pin bearing part may be a complete sphere (except for the place at which it joins the pin). The spherical pin bearing part may be spherical over a sufficiently large part of its outer surface that during the movement of the part of the sleeve a spherical surface of the pin bearing part remains in contact with the bearing cavity. The spherical pin bearing part may comprise an integral part of the pin, or alternately, e.g. to minimise the effect of wear on the spherical pin bearing part the part may be made of metal as a separate part and attached to the pin.

Typically the pin bearing receiving cavity may comprise a slot or other shaped aperture in a surface of the bristle carrier radially outward from the rotation axis of the bristle carrier. The pin bearing receiving cavity is dimensioned such that as the pin bearing part moves reciprocally transversely as the head drive shaft moves in oscillatory rotary motion, the pin bearing part bears upon side surfaces of the cavity which are circumferentially spaced around the rotation axis of the bristle carrier, so as to cause the bristle carrier to move in response in oscillatory rotary motion.

The bristle carrier has a surface from which the bristles extend. It is preferred that side of the pin bearing receiving cavity furthest from this surface is closed or constricted so that in the event of a force being applied to the bristle carrier tending to remove it from the bristle carrier mounting the bristle carrier abuts against the pin and/or pin bearing part to resist such force. This can help retain the bristle carrier on the mounting. This construction can improve the so called "pull strength" of the bristle carrier, in accordance with the safety requirements of some countries. Often in powered toothbrush heads it is known to provide a retainer pin in the bristle carrier mounting engaging with a cavity in the bristle mounting to help retain the bristle carrier on the bristle carrier mounting, and the aforementioned closing or constriction of the cavity can supplement the action of such a retainer pin.

Typically the bristle carrier may be made of a plastic material, such as POM (polyoxymethylene), and may be made by injection moulding with the cavity formed during the moulding process. This bearing receiving cavity may also be plastic sided, or may be lined with metal.

The bristle carrier may be generally cylindrical about its rotation axis. Typically the bristle carrier may be mounted in the bristle carrier mounting with an axle between the mounting and the bristle carrier. Typically such an axle is a metal pin axle.

The term "bristle" and derived terms herein refers to all kinds of oral cleaning elements, for example filament bristles such as made of nylon or PBT (polybutyleneterphthalate), which may for example be cylindrical with rounded ends, or may be tapered as for example disclosed in EP-B-0 596 633 B1. Alternatively such elements may be made of elastomer materials, such as fingers, strips, lamellae etc., for example of types known in the art. Combinations of such elements may be used.

Other parts of the toothbrush head of this invention may be otherwise conventional.

The connection may for example be a known type of push fit, screw fit or bayonet connection suitable to connect with a corresponding connector on a toothbrush handle, such as the type well known from Oral-B™ electric toothbrushes. The connection may comprise an insertable adaptor to adapt the internal profile of the sleeve to the external profile of the connector, for example as disclosed in U.S. Pat. No. 3,369,265.

The toothbrush head part of this invention is suitable for use with known types of toothbrush handle which contain an electric power source such as a replaceable or rechargeable battery and an electric motor powered by the power source. Typically such handles have a drive shaft which extends from the handle and which can be made to rotate with oscillatory rotary motion, and which connects with the head part drive shaft.

The invention will now be described by way of example only with reference to the accompanying drawings.

Figure 1:
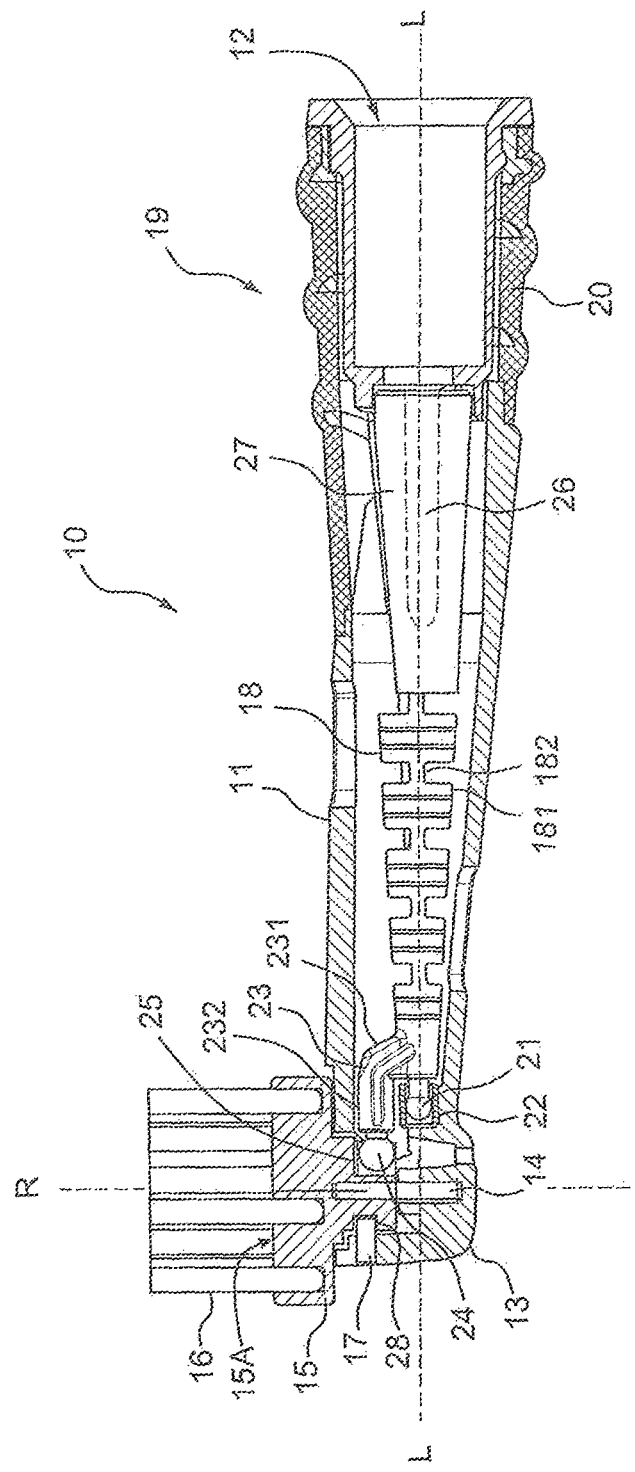
FIG. 1 shows a longitudinal sectional view of a toothbrush head of this invention.
Figure 3:
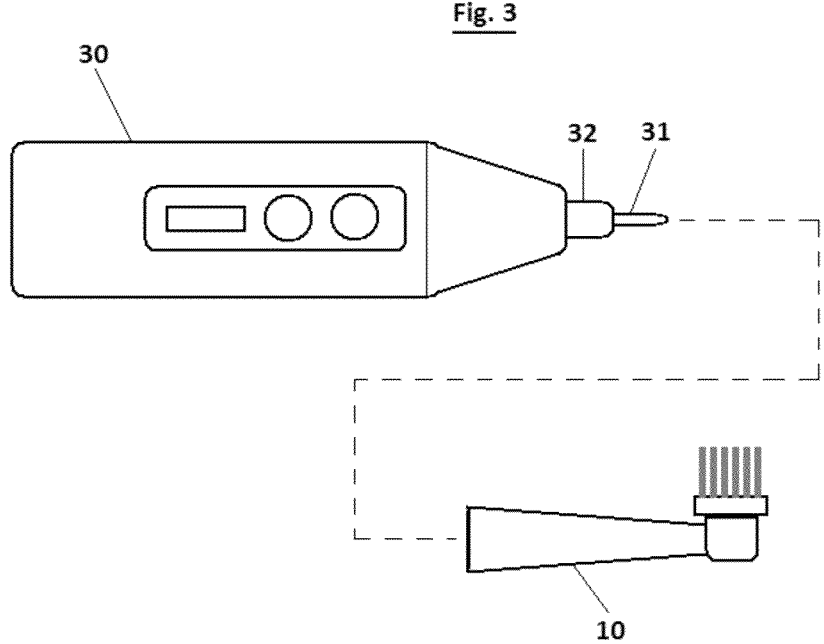

FIG. 3 shows how the toothbrush head engages with a toothbrush handle. Referring to FIG. 1 this shows generally a toothbrush head part of the invention 10, comprising an elongate hollow sleeve 11 having a longitudinal direction L-L, and having a connection 12 at one longitudinal end to mate with a connector (not shown, see FIG. 3) on an electric toothbrush handle (not shown, see FIG. 3), this connection 12 being a conventional bayonet or push fit connection.

At the opposite end of sleeve 11 is a bristle carrier mounting 13, comprising an axle 14 on which is mounted a bristle carrier 15 able to rotate on the axle about a rotation axis R-R defined by the axle 14 and being transverse to the sleeve longitudinal direction L-L. On surface 15A of the bristle carrier 15 are mounted bristles 16, extending in the direction parallel to the rotation axis R-R. A retainer pin 17 engages with a circumferential slot 28 in the bristle carrier 15 to retain the bristle carrier 15 on the mounting 13, and also limits the rotation of the bristle carrier 15 on axle 14 so that the rotation of the bristle carrier 15 is limited to oscillatory rotary motion. This overall construction is conventional.

A head drive shaft 18 extends longitudinally along and within the sleeve part 11 and is mounted for oscillatory rotary motion within sleeve 11 about a rotation axis coaxial with the sleeve 11 longitudinal direction L-L.

The sleeve 11 incorporates a flexible region 19 which allows the part of the sleeve between the bristle support 13 and the flexible region 19 to move relative to the connection 12 under pressure on the bristle carrier 15 during use. Flexible region 19 comprises a composite plastics material—elastomer material region, provided by the sleeve 11 being made of a plastics material such as polypropylene having apertures in the plastic material of the sleeve containing a thermoplastic elastomer material 20. The flexible region 19 extends from the end of the sleeve 11 closest to the connection 12 for ca. 30% of the distance between the connection 12 and the bristle carrier mounting 13. The flexible region 19 allows the part of the sleeve 12 between the bristle support 13 and flexible region 19 to move relative to the connection 12 under pressure on the bristle carrier 15 during use in an arc in a plane parallel to the rotation axis R-R of the bristle carrier 15, i.e. in the plane of the drawing.

The head drive shaft 18 is made of a flexible plastic material, such as POM (polyoxymethylene). The head drive comprises longitudinally alternating wide 181 and narrow 182 portions to enhance flexibility, i.e. encouraging bending about the narrow portions 182.

Adjacent the end of the head drive shaft 18 longitudinally furthest from the connection 12 is a spherical head drive shaft bearing part 21. The sleeve 12 has a corresponding head drive shaft bearing part receiving cavity 22 receiving the bearing part 21. The bearing part 21 is provided in the form of a metal pin set in the end of the shaft 18, with its end remote from the shaft 18 formed into a spherical shape. The cavity 22 is provided in the form of a metal cylinder of internal cylindrical bore closely corresponding to the outer diameter of the spherical bearing part 21.

The head part 10 incorporates a transmission system to convert the oscillatory rotation of the head drive shaft 18 into oscillatory rotation of the bristle carrier 15 about the rotation axis R-R transverse to the shaft longitudinal direction L-L. This transmission system comprises an eccentric pin 23 extending integrally from the head drive shaft 18 adjacent the end of the head drive shaft 18 longitudinally furthest from the connection 12. This pin 23 comprises a first part 231 close to the shaft 18 which extends transverse to the longitudinal direction L-L, then a second part 232 extending parallel to the longitudinal direction to a pin end 24 distanced from the head drive shaft 18 in a direction radial to the rotation axis of the head drive shaft 18. This pin end 24 is in the form of a spherical pin bearing part, being a metal pin set into the end of the part 232, with its end remote from the connection 12 formed into a spherical shape.

In a surface of the bristle carrier 15 radially distanced from the rotation axis R-R is a spherical pin bearing part receiving cavity 25 to receive the spherical pin bearing part 24. The cavity 25 is dimensioned such that when the head drive shaft 18 moves in oscillatory rotary motion about its rotation axis L-L the spherical pin bearing part 24 bears alternatingly against side surfaces of the cavity circumferentially spaced around the rotation axis R-R of the bristle carrier 15 such that the bristle carrier 15 is thereby caused to move in oscillatory rotary motion about axis R-R.

At the end of the head drive shaft 18 a spline socket 26 (shown schematically) is formed within an integrally widened part 27, capable of engaging in a conventional manner with the drive shaft (not shown, see FIG. 3) of a toothbrush handle (not shown, see FIG. 3).

Figure 2:
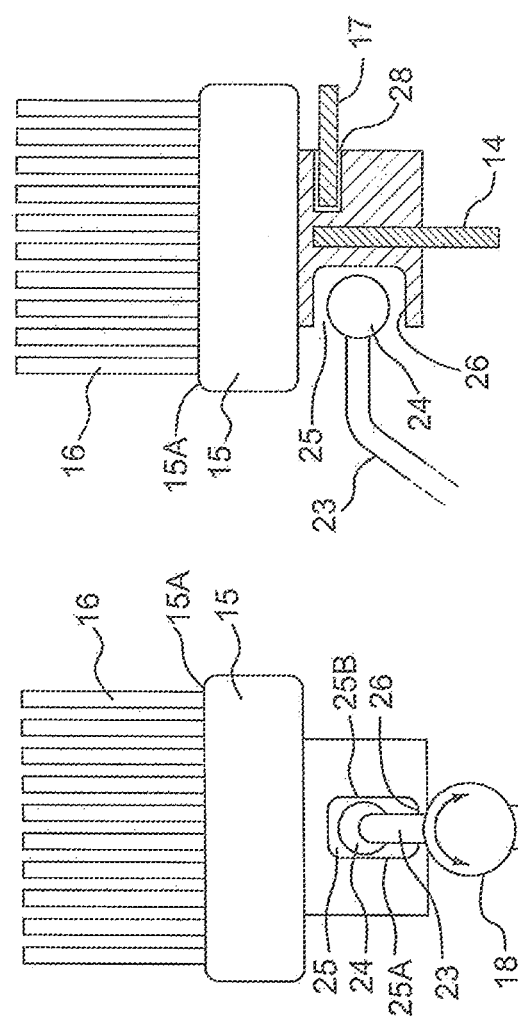
FIG. 2A and FIG. 2B show the transmission system in two schematic views along and across the longitudinal direction.

FIG. 2 is a schematic diagram of the operation of the transmission system of the toothbrush head part of FIG. 1. Two views are shown looking respectively along and across the longitudinal axis L-L. As the head drive shaft 18 rotates in oscillatory rotary motion about its axis L-L the eccentric pin 23 swings from side to side, and the spherical pin bearing part 24 bears alternatingly against side surfaces 25A, 25B of the cavity 25, spaced apart circumferentially around the rotation axis R-R. This causes the bristle carrier 15 to correspondingly move in oscillatory rotary motion about its own rotation axis R-R.

It is seen that because of the spherical bearing parts 21, 24, no matter how much the shaft 17 and the head drive shaft 18 flex under pressure during toothbrushing, and consequently cause the bearing parts 21,24 to move in bearing respective bearing cavities 22,25, a spherical surface of the parts 21, 24 remains in contact with the respective cavities 22, 25. Consequently, drive forces and friction between the head drive shaft 18 and the cavity 22, and between the pin 23 and the cavity 25 of the bristle carrier 15 is maintained suitably constant, minimizing wear and vibration during use.

FIG. 2 also shows how the side 26 of the pin bearing receiving cavity 25 furthest from the surface 15A from which bristles 16 extend is closed by wall part 26. It will be seen from FIG. 2 that in the event of a force being applied to the bristle carrier 15 tending to remove it from the bristle carrier mounting (not shown in FIG. 2) the wall part 26 of bristle carrier 15 will abut against the pin bearing part 24 to resist such force and to help retain the bristle carrier 15 on the mounting, supplementing the action of the retainer pin 17 in its slot 28.

FIG. 3 shows schematically how the toothbrush head 10 engages with the handle 30 of a power toothbrush. The handle 30 contains an electric power source such as a replaceable or rechargeable battery (not shown) and an electric motor (not shown) powered by the power source. From handle 30 extends a handle drive shaft 31, there being a transmission means (not shown) between the motor and the handle drive shaft to cause the drive shaft 31 to rotate with oscillatory rotary motion. Adjacent the handle drive shaft 31 is a connector 32 for the replaceable head part 10, the handle drive shaft 31 passing through the connector 32. In use the connector 32 engages in a male-female cooperation with connection 12 of the toothbrush head 10, and when so connected the drive shaft 31 engages in a male-female cooperation with the socket 26 so that drive shaft 31 can drive shaft 18.

The invention claimed is:

1. A replaceable head part for an electric powered toothbrush comprising an elongate sleeve having a connection at one longitudinal end to mate with a connector on an electric toothbrush handle, the sleeve having a bristle support mounting at the opposite longitudinal end and having a bristle carrier mounted thereon for rotary motion about a rotation axis transverse to the sleeve longitudinal direction, having a head drive shaft extending longitudinally along the sleeve part and mounted for rotary motion about a rotation axis generally aligned with the sleeve longitudinal direction, characterized in that:

the sleeve incorporates a flexible region which allows the part of the sleeve between the bristle support and flexible region to move relative to the connection under pressure on the bristle carrier during use, adjacent the end of the head drive shaft longitudinally furthest from the connection is a spherical head drive shaft bearing part, and the sleeve has a corresponding head drive shaft bearing part receiving cavity receiving the spherical head drive shaft bearing part, the head part incorporates a transmission system to convert the rotation of the head drive shaft into rotation of the bristle carrier about a rotation axis transverse to the shaft longitudinal direction comprising an eccentric pin extending from the head drive shaft adjacent the end of the head drive shaft longitudinally furthest from the connection to a pin end distanced from the head drive shaft in a direction radial to the rotation axis of the head drive shaft, and having adjacent to the pin end a spherical pin bearing part, the bristle carrier having a spherical pin bearing part receiving cavity therein radially distanced from the rotation axis of the bristle carrier, to receive the spherical pin bearing part, and dimensioned such that when the head drive shaft moves in oscillatory rotary motion about its rotation axis the spherical pin bearing part bears against surfaces of the cavity circumferentially spaced around the rotation axis of the bristle carrier such that the bristle carrier is thereby caused to move in oscillatory rotary motion.

2. A replaceable head part according to claim 1 wherein the bristle carrier is mounted for oscillatory rotary motion.

3. A replaceable head part according to claim 1 wherein the rotation axis of the bristle carrier is within 80-90° to the sleeve longitudinal direction.

4. A replaceable head part according to claim 1, wherein the head drive shaft is mounted for oscillatory rotary motion.

5. A replaceable head part according to claim 1 wherein the flexible region is located in the longitudinal half of the sleeve closest to the connection.

6. A replaceable head part according to claim 1 wherein the flexible region allows the part of the sleeve between the bristle support and flexible region to move relative to the connection under pressure on the bristle carrier during use in an arc in a plane parallel to the rotation axis of the bristle carrier.

7. A replaceable head part according to claim 1 wherein the head drive shaft is flexibly able to bend as the said part of the sleeve moves.

8. A replaceable head part according to claim 7 wherein the head drive shaft is made of a flexible plastics material and the spherical head drive shaft bearing part is made of metal as a separate part and attached to the drive shaft.

9. A replaceable head part according to claim 8 wherein the head drive shaft bearing part receiving cavity is metal-lined and provided by a cylindrical bored insert into the plastic material of the sleeve.

10. A replaceable head part according to claim 1 wherein the head drive shaft bearing part receiving cavity which receives the spherical bearing part adjacent the end of the drive shaft is a cylindrical cavity.

11. A replaceable head part according to claim 1 wherein the eccentric pin comprises a pin part extending transverse to the head drive shaft in a direction radial to the rotation axis of the head drive shaft, connecting to a pin part extending parallel to the head drive shaft to the pin end.

12. A replaceable head part according to claim 1 wherein the spherical pin bearing part is made of metal as a separate part and attached to the pin.

13. A replaceable head part according to claim 1 wherein the bearing receiving cavity comprises an aperture in a surface of the bristle carrier radially outward from the rotation axis of the bristle carrier.

14. A replaceable head part according to claim 13 wherein the bearing receiving cavity is plastic sided, or lined with metal.

15. A replaceable head part according to claim 1 wherein the side of the pin bearing receiving cavity furthest from the surface of the bristle carrier from which bristles extend is closed or constricted so that in the event of a force being applied to the bristle carrier tending to remove it from the bristle support the bristle carrier abuts against the pin and/or pin bearing part to resist such force.

16. A power toothbrush comprising a handle containing an electric power source such as a replaceable or rechargeable battery and an electric motor powered by the power source in combination with a replaceable head part as claimed in claim 1.

* * * * *